US012042381B2

(12) United States Patent
Zimmermann et al.

(10) Patent No.: US 12,042,381 B2
(45) Date of Patent: Jul. 23, 2024

(54) POUCH-LIKE CONSTRUCT FOR PREVENTING HEART DISTENSION

(71) Applicant: UNIVERSITATSKLINIKUM HAMBURG-EPPENDORF, Hamburg (DE)

(72) Inventors: Wolfram-Hubertus Zimmermann, Hamburg (DE); Thomas Eschenhagen, Hamburg (DE); Yalin Yildirim, Hamburg (DE)

(73) Assignee: Tissue Systems Holding GmbH, Göttingen (DE)

( * ) Notice: Subject to any disclaimer, the term of this patent is extended or adjusted under 35 U.S.C. 154(b) by 380 days.

(21) Appl. No.: 16/677,323

(22) Filed: Nov. 7, 2019

(65) Prior Publication Data

US 2020/0197177 A1 Jun. 25, 2020

Related U.S. Application Data

(60) Division of application No. 15/272,022, filed on Sep. 21, 2016, now Pat. No. 10,500,051, which is a continuation of application No. 14/324,856, filed on Jul. 7, 2014, now abandoned, which is a continuation of application No. 12/514,431, filed as application No. PCT/EP2007/062183 on Nov. 11, 2007, now abandoned.

(30) Foreign Application Priority Data

Nov. 11, 2006 (EP) .................................... 06400036

(51) Int. Cl.
*A61L 27/38* (2006.01)
*A61F 2/24* (2006.01)
*A61K 35/34* (2015.01)
*A61L 27/54* (2006.01)

(52) U.S. Cl.
CPC ............ *A61F 2/2481* (2013.01); *A61K 35/34* (2013.01); *A61L 27/38* (2013.01); *A61L 27/54* (2013.01); *A61F 2240/001* (2013.01); *A61L 2300/412* (2013.01); *A61L 2300/414* (2013.01)

(58) Field of Classification Search
None
See application file for complete search history.

(56) References Cited

U.S. PATENT DOCUMENTS

| | | | |
|---|---|---|---|
| 1,387,293 | A | 8/1921 | Morse |
| 3,610,563 | A | 10/1971 | Allen |
| 5,702,343 | A | 12/1997 | Alferness |
| 6,416,459 | B1 | 7/2002 | Haindl |
| 2003/0091979 | A1 | 5/2003 | Eschenhagen |
| 2005/0085688 | A1 | 4/2005 | Girard et al. |

FOREIGN PATENT DOCUMENTS

| | | |
|---|---|---|
| EP | 1783206 A1 | 5/2007 |
| WO | WO-2002/19893 | 12/2002 |

OTHER PUBLICATIONS

Akins et al., Cardiac organogenesis in vitro: reestablishment of three-dimensional tissue architecture by dissociated neonatal rat ventricular cells, *Tissue Eng.* 5(2): 103-18 (1999).
Badorff et al., Transdifferentiation of blood-derived human adult endothelial progenitor cells into functionally active cardiomyocytes, *Circulation* 107: 1024-32 (2003).
Beltrami et al., Adult cardiac stem cells are multipotent and support myocardial regeneration, *Cell* 114: 763-6 (2003).
Blom et al., Cardiac support device modifies left ventricular geometry and myocardial structure after myocardial infarction, *Circulation* 112: 1274-83 (2005).
Boiani et al., Activity of the germline-specific Oct4-GFP transgene in normal and clone mouse embryos, *Methods Mol. Biol.* 254: 1-34 (2004).
Bursac et al., Cardiac muscle tissue engineering: Toward in vitro model for electrophysiological studies, *Am. J. Physiol. Heart Circ. Physiol.* 277: H433-4 (1999).
Carrier et al., Cardiac tissue engineering: Cell seeding, cultivation parameters, and tissue construct characterization, *Biotechnol. Bioeng.* 64: 580-9 (1999).
Cowan et al., Nuclear reprogramming of somatic cells after fusion with human embryonic stem cells, *Science* 309: 1369-7 (2005).
Dimmeler et al., Unchain my heart: the scientific foundations of cardiac repair, *J. Clin. Invest.* 115: 572-83 (2005).
Eiges et al., Establishment of human embryonic stem cell-transfected clones carrying a marker for undifferentiated cells, *Curr. Biol.* 11: 514-8 (2001).
Eschenhagen et al., 3D engineered heart tissue for replacement therapy, *Basic Res. Cardiol.* 97:(Suppl. 1)1/146-1/152 (2002).
Eschenhagen et al., Three-dimensional reconstitution of embryonic cardiomyocytes in a collagen matrix: a new heart muscle model system, *FASEB J.* 11: 683-94 (1997).
Fink et al., Chronic stretch of engineered heart tissue induces hypertrophy and functional improvement, *FASEB. J.* 14: 669-79 (2000).
Freed et al., Advanced tools for tissue engineering: scaffolds, bioreactors, and signaling, *Tissue Engineering* 12(12): 3285-305 (2006).
Guan et al., Pluripotency of spermatogonial stem cells from adult mouse testis, *Nature* 440: 1199-203 (2006).
Hosler et al., An octamer motif contributes to the expression of the retinoic acid-regulated zinc finger gene Rex-1 (Zfp-42) in F9 teratocarcinoma cells, *Mol. Cell. Biol.* 13:2919-28 (1993).

(Continued)

*Primary Examiner* — Emily A Cordas
(74) *Attorney, Agent, or Firm* — MARSHALL, GERSTEIN & BORUN LLP (57) ABSTRACT

The invention is directed to a pouch-like construct comprising mammalian tissue which can be used for preventing distension and/or resisting dilation of the heart in a mammal. Preferably, the pouch-like tissue construct has contractile properties. The invention further relates to a method for the preparation of a pouch-like construct comprising mammalian tissue which can be used for the above purposes.

18 Claims, 6 Drawing Sheets

(56) References Cited

OTHER PUBLICATIONS

International Preliminary Report on Patentability, PCT/EP2007/062183, dated May 12, 2009.
Jackson et al., Regeneration of ischemic cardiac muscle and vascular endothelium by adult stem cells, *J. Clin. Invest.* 107(11): 1395-1402 (2001).
Kehat et al., Human embryonic stem cells can differentiate into myocytes with structural and functional properties of cardiomyocytes, *J. Clin. Invest.* 108: 407-14 (2001).
Klimanskaya et al., Human embryonic stem cell lines derived from single blastomeres, *Nature Lett.* 444(23): 481-5 (2006).
Klug et al., Genetically selected cardiac myocytes from differentiating embryonic stem cells from stable intracardiac grafts, *J. Clin. Invest.* 98: 216-24 (1996).
Laugwitz et al., Postnatal is11+ cardioblasts enter fully differentiated cardiomyocyte lineages, *Nature Lett.* 433: 647-53 (2005).
Leor et al., Bioengineered cardiac grafts: a new approach to repair the infracted myocardium? *Circulation* 102:111-56-61 (2000).
Leor et al., Cells, scaffolds, and molecules for myocardial tissue engineering, *Pharmacology & Therapeutics* 105: 151-63 (2005).
Li et al., Survival and function of bioengineered cardiac grafts, *Circulation* 100: 11-63-69 (1999).
Liau et al., Functional cardiac tissue engineering, *Journal of Regenerative Medicine* 7(2): 187-206 (2012).
Lockett et al., Relative efficiency of tumor cell killing in vitro by two enzyme-prodrug systems delivered by identical adenovirus vectors, *Clin. Cancer. Res.* 3: 2075-80 (1997).
Ma et al., High-level sustained transgene expression in human embryonic stem cells using lentiviral vectors. *Stem Cells* 21: 111-7 (2003).
Mikos et al., Engineering complex tissues, *Tissue Engineering* 12(12): 3307-39 (2006).
Muller et al., Selection of ventricular-like cardiac myocytes from ES cells in vitro, *FASEB J.* 14: 2540-8 (2000).
Mummery et al., Differentiation of human embryonic stem cells to cardiac myocytes: role of co-culture with visceral endoderm-like cells, *Circulation* 107: 2733-40 (2003).
Murry et al., Cell-based cardiac repair: reflections at the 10-year point, *Circulation* 112: 3174-83 (2005).
Naito et al., Optimizing engineered heart tissue for therapeutic applications as surrogate heart muscle. *Circulation* 114 (1 Supplement): 172-8 (2006).
Oh et al., Cardiac progenitor cells from adult myocardium: homing, differentiation, and fusion after infarction. *Proc. Natl. Acad. Sci. USA* 100(21): 12313-8 (2003).
Scholz, Cell adhesion and growth on coated or modified glass or plastic surfaces, *Nalge NUNCTM Bulletin.* 13, No. 41187 (2003).
Schroder et al., Cardiac transplantation following ACORN CorCap device implantation. *Eur. J. Cardiothorac. Surg.* 29: 848-50 (2006).
Shimizu et al., Fabrication of pulsatile cardiac tissue grafts using a novel 3-dimentional cell sheet manipulation technique and temperature-responsive cell culture surface, *Circ. Res.* 90: E40-8 (2002).
Stevens et al., Physiological function and transplantation of scaffold-free and vascularized human cardiac muscle tisse, *Proc. Natl. Acad. Sci. USA* 106(39): 16568-73 (2009).
Takahashi et al., Induction of pluripotent stem cells from mouse embryonic and adult fibroblast cultures by defined factors, *Cell* 126: 663-76 (2006).
Thomson et al., Embryonic stem cell lines derived from human blastocysts, *Science* 282: 1145-7 (1998).
Van Luyn et al., Cardiac tissue engineering: Characteristics of in unison contracting two- and three-dimensional neonatal rat ventricle cell (co)-cultures, *Biomaterials* 23: 4793-801 (2002).
Vrana et al., Nonhuman primate parthenogenetic stem cells, *Proc. Natl. Acad. Sci. USA* 100(Suppl. 1): 11911-6 (2003).
Wakayama et al., Differentiation of embryonic stem cell lines generated from adult somatic cells by nuclear transfer, *Science* 292: 740-3 (2001).
Written Opinion of the International Searching Authority, PCT/EP2007/062183, dated Dec. 13, 2007.
Xu et al., Characterization and enrichment of cardiac myocytes derived from human embryonic stem cells, *Circ. Res.* 91: 501-8 (2002).
Zimmermann et al., Cardiac grafting of engineered heart tissue in syngenic rats, *Circulation* 106: 1151-7 (2002).
Zimmermann et al., Cardiac tissue engineering for replacement therapy, *Heart Failure Rev.* 8: 259-69 (2003).
Zimmermann et al., Engineered heart tissue for regeneration of diseased hearts, *Biomaterials* 25: 1639-47 (2004).
Zimmermann et al., Engineered heart tissue grafts improve systolic and diastolic function ini nfarcted rat hearts, *Nat. Med.* 12: 452-8 (2006).
Zimmermann et al., Three-dimensional engineered heart tissue from neonatal rat cardiac myocytes, *Biotechnol. Bioeng.* 68: 106-14 (2000).
Zimmermann et al., Tissue engineering of a differentiated cardiac muscle construct, *Circ. Res.* 90: 223-30 (2002).

A) Heart of a neonatal rat  C) Spheroidal EHT
B) EHT                      D) Heart of an adult rat

POUCH-LIKE CONSTRUCT FOR PREVENTING HEART DISTENSION

FIELD OF THE INVENTION

The invention is directed to a pouch-like construct comprising mammalian tissue which can be used for preventing distension and/or resisting dilation of the heart in a mammal. Preferably, the pouch-like tissue construct has contractile properties. The invention further relates to a method for the preparation of a pouch-like construct comprising mammalian tissue which can be used for the above purposes.

BACKGROUND OF THE INVENTION

Cardiac dilation is a common clinical phenomenon observed in several cardiac diseases, such as post-myocardial infarction and heart failure. In an early stage of cardiac dilation, the organ enlargement may be restricted to only a portion of the heart, such as the left ventricle. In an advanced stage, the complete heart may be enlarged. With each type of cardiac dilation, serious problems are associated which may include arrhythmias or leakage of the cardiac valves. Cardiac dilation is a frequent reason for subjecting a patient to heart transplantation.

Drugs (e.g. beta-adrenoceptorblockers, angiotensin converting enzyme inhibitors, aldosterone antagonists, digoxin, diuretics) are frequently employed for treating problems associated with cardiac dilation and heart failure. Yet, drugs can at best delay the natural progression of most cardiac diseases. Complete healing of myocardial dilation or heart failure has not been achieved so far.

Recently, passive ventricular restraint devices (e.g. Cor-Cap Cardiac Support Device; Acorn Cardiovascular Inc., St. Paul, Minn., USA) have been applied to stop adverse LV remodelling and dilation in failing hearts, (Blom et al. (2005). Circulation; 112:1274-83). International application WO 98/58598, for example, describes an elastic plastic bag for avoiding an excessive dilation of the heart beyond a critical volume. U.S. Pat. No. 5,702,343 discloses a jacket for constraining cardiac expansion during diastole. US Patent application 2005/0085688 describes an elastic cardiac support device of a biocompatible material for constraining expansion of the heart without interfering with systolic contraction. Despite positive trials in Europe and North America, the use of cardiac support devices (CSD) has recently been stopped by the U.S. Food and Drug Administration due to safety concerns. It has been found that pericardial constriction may occur in patients with cardiac support devices making reoperations necessary which are technically challenging (Schroder et al. (2006), Eur J Cardiothorac Surg; 29:848-50).

The ex vivo-production of heart tissue by tissue engineering offers an alternative approach of preventing cardiac dilation and heart failure. Tissue engineering aims at generating functional three-dimensional tissues that can be tailored in size, shape and function according to the respective needs before implanting them into the body. Therapeutically applied artificial heart tissue should stabilize the failing heart to prevent further dilation and in addition add contractile elements to a dilated or failing heart. Several publications describe the in vitro generation of engineered myocardium in different geometrical sizes and shapes (Akins R E, et al. (1999), Tissue Eng, 5:103-18; Bursac N, et al. (1999), Am J Physiol, 277:H433-44; Carrier R L, et al. (1999), Biotechnol Bioeng; 64:580-9; Eschenhagen T, et al. (1997), Faseb J, 11:683-94; Leor J, et al. (2000). Circulation, 102:111 56-61; Li R K, et al. (1999). Circulation, 100:11 63-9; Shimizu T, et al. (2002). Circ Res, 90:E40; van Luyn M J, et al. (2002) Biomaterials, 23:4793-801; Zimmermann W H, et al. (2002). Circ Res., 90:223-30; Zimmermann W H, et al., (2000), Biotechnol Bioeng, 68:106-14). Engineered heart tissue can be reconstituted by mixing heart cells from rat (including cardiac myocytes, fibroblasts, smooth muscle cells, endothelial cells, macrophages and other cells of leukocytic origin, etc.) with collagen type I, MATRIGEL™ and culture medium, European application 05400038.5 describes the generation of engineered human heart tissue constructs derived from stem cells.

However, the generation of engineered tissue is technically challenging, since the size of the constructs appears to be limited by the maximum diffusion distances for nutrients and oxygen. Therefore, it was not possible so far to construct larger three-dimensional tissue constructs which are suitable to be used for stabilizing a large mammalian heart suffering from cardiac dilation.

DESCRIPTION OF THE FIGURES

FIG. 2 shows a further schematic depiction of the method of the invention. The sketch on the top (FIG. 2A) demonstrates the casting of a pouch-like myocardial tissue construct. EHT components comprise: 1) neonatal rat heart cells ($10 \times 10^6$), 2) rat tail collagen type I (0.8=imp, 3) MATRIGEL™ (10% v/v), and 4) serum containing culture medium. The pictures (FIG. 2B) on the bottom are photographs of the pouch-like myocardial tissue construct. The top picture (labeled day 3) shows a complete casting mold filled with culture medium and the inner glass spacer covered by a pouch-like myocardial tissue construct. The middle picture (labeled day 7) demonstrates two pouch-like myocardial tissue constructs being resiliently based on two metal holders to facilitate auxotonic contractions of the constructs. The bottom picture (labeled day 12) demonstrates a pouch-like myocardial construct in an isometric contraction experiment to define its contractility.

DESCRIPTION OF THE INVENTION

It has now been found in the course of the present invention that it is possible to prepare a large pouch-like construct, i.e. a bag-shaped structure having an opening and preferably a single opening, which comprises mammalian tissue, preferably human tissue. The construct is shaped in such a manner that it is suitable for enclosing and compressing at least part of the heart of a mammal. This means that the pouch-like construct is adapted to receive the heart of a mammal in such a manner that a slight pressure is applied by the pouch-like construct on the surface of the heart, which pressure prevents distension and/or resists dilation during systolic and diastolic activity of the heart. Preferably, the construct embraces the ventricles of the heart, which means that when applied to the surface of the heart, the construct reaches from the *Apex cordis* to the *Sulcus coronarius* cordis which is the annular groove located between the ventricles and the atria. Preferably, the construct is to be applied to the outer surface of the heart such that it is in direct contact with the epicardium of the heart. This procedure requires the removal of the pericardium. Alternatively, the pericardium can remain intact and the pouch-like myocardial tissue construct can be applied on its outer surface. Another alternative is to manually roughen/injure the epicardium before applying the construct to facilitate direct contact to the myocardium. The construct has in either case, and specially after removal of the pericardium, the capability to structurally integrate into the myocardium. In a preferred embodiment of the invention, the construct is adapted to be applied to a heart from a dog, cat, sheep, primate or a human.

The pouch-like construct of the invention has structural properties which render it highly suitable for use as a biologically compatible cardiac support device to reduce and/or prevent cardiac dilation in a mammal suffering from such condition. The construct may consist of mammalian tissue or it may comprise such mammalian tissue. For example, it may consist of a three-dimensional support material to which individual portions of engineered mammalian tissue adhere. These portions can be fused together at a later stage of the preparation process to form the final tissue construct. Preferably, the support materials are designed such that they degrade as the individual tissue portions fuse together. Suitable support materials are known in the art and comprise, for example, collagen, silk proteins, and highly elastic glycerol-polymers (such as "Biorubber"). Preferably, the pouch-like construct consists of mammalian tissue. Preferably, the mammalian tissue is engineered tissue, i.e. tissue generated by in-vitro tissue engineering techniques. It is particular preferred that the mammalian engineered tissue is engineered heart tissue. As used herein, the term "engineered heart tissue" means a tissue of mammalian origin, preferably of human or primate origin, which comprises mammalian cardiac myocytes and has been obtained by tissue engineering techniques. As used herein, the terms "cardiac myocyte" and "cardiomyocyte" are used interchangeably and refer to a cell composed of myofibrils that provide contractile force when stimulated. Apart from cardiac myocytes, heart tissue can also comprise fibroblasts, endothelial cells, smooth muscle cells, macrophages and other cells of mononuclear origin.

Preferably, the pouch-like construct comprises or consists of mammalian tissue comprising cardiac myocytes. Typically, the presence of cardiac cells within a tissue construct can be confirmed by positive staining with anti-cardiac myosin heavy chain, anti-α-actinin, anti-desmin and/or anti-cardiac troponin I antibodies (see Kehat I. et al. (2001), J Clin Invest 108, 407-14). More than 25% of the volume of the pouch-like construct may consist of cardiac myocytes. Preferably, these tissues are designed such that they confer contractile properties to the construct. The in-vitro generation of contractile engineered heart tissue comprising cardiac myocytes has been extensively described in the art, for example in Zimmermann W H, et al. (2002). Circ Res., 90:223-30; Zimmermann W H, et al. (2000), Biotechnol Bioeng, 68:106-14, or in international application WO 01/55297. Here, it was shown that three-dimensional contractile heart muscle constructs can be obtained from mammalian cardiac myocytes. The pouch-like constructs of the present invention may be prepared according to the same reconstitution mixture and protocols disclosed in these publications. Due to their unique shape, the constructs advantageously offer structural support (restraint) as well as functional support (contractility) to failing hearts. The constructs according to the invention preferably have a wall thickness of 1-8 mm, more preferably 2-3 mm. Due to the considerably low thickness of the constructs, it is possible to use a plurality of these constructs nested one in the other in an onion-like fashion.

In general, the pouch-like constructs of the invention can be generated from muscle and non-muscle cells as well as from mixtures of muscle and non-muscle cells. Muscle cells may include primary and stem cell derived cardiac myocytes as well as primary and stem cell derived skeletal and smooth muscle cells. These cell types would either actively support myocardial contractility by conferring force of contraction to the heart or offer passively structural support to the heart. For example, cardiac myocytes obtained from cell samples of hearts of different mammals, such as rat, mouse, primates or human, may be used for preparing the contractile engineered tissue, as described in Zimmermann, et al. Circ Res 90, 223-30 (2002) and International application WO 01/55297. Preferably, fetal or neonatal cardiac myocytes are used for engineering the tissue constructs. These cells are particularly suitable, since they have the capability to redifferentiate after dedifferentiation. It has also been shown that mixed populations consisting of almost identical portions of cardiac myocytes and non-cardiac myocytes result in engineered tissues with increased contractile properties compared to selected cardiac myocytes (Zimmermann et al. (2003), Heart Failure Rev., 8, 259-269).

Briefly, a solution of a scaffold substance (such as collagen type I) is mixed with culture medium (final concentration in the mixture: 1.times.DMEM; 2% chicken embryo extract; 10% horse serum; 100 g/ml Streptomycin; 100 U/ml penicillin). The pH of the mixture is adjusted to a physiologic pH value of about 7.4 with 0.1 N NaOH. Engelbreth-Holm-Swarm tumor exudate (known as "MATRIGEL™") is added to give a final concentration of 5-15%. This mixture is added to a cell suspension of fetal or neonatal cells (for example, $2.5 \times 10^6$ cells/engineered heart tissue). The reconstitution mixture is incubated for 0.5-3 h, preferably for 1 h, at 37° C. in a humidified cell culture incubator (5-10% $CO_2$ in room air) to facilitate hardening. The resulting tissue construct is further cultured in a suitable medium. In this step, which has been used for casting the tissue construct, Suitable culturing conditions are described in the art and comprise a physiological temperature range of 30-40° C., preferably 36-38° C., and more preferably 37° C. The percentage of $O_2$ in the ambient air should range from 21-80%, preferably 70%, 60%, 50%, and more preferably 40%. Culturing may be performed for 3 to 50 days, preferably 10-30 days, and more preferably 15-20 days.

It has been shown that the MATRIGEL™ in the medium may be substituted against insulin and triiodothyronine in order to provide a more defined medium. The addition of insulin (for example, 10 □g/ml) and triiodothyronine (for example 1 nM) allowed for the generation of strongly contracting engineered tissues. Simultaneous addition of both factors for only 24 h at the beginning of the tissue culture was sufficient. By using insulin and triiodothyronine during tissue construction, improved contractility was achieved with the engineered heart tissues. These effects did not stem from enhanced overall cell number in the engineered tissues, since no difference in the DNA content and no apparent structural differences were observed. Rather, the effects may be the result of enhanced protein content or improved survival of cardiac myocytes leading to a higher cardiac myocyte fraction without an apparent change of the overall cell number.

Additionally, the culturing of the engineered tissues of the invention may also be performed by use of media as described above, wherein the serum is replaced (e.g. by ESC) Culturing may also be performed in serum-free media. A serum-free medium suitable for culturing the cardiac myocytes is exemplified in Table 1. The person skilled in the art will readily be able to further modify the medium on the basis of the disclosure provided herein by replacing distinct components and/or growth factors by similar substances,

TABLE 1

| Serum-free culture medium | |
|---|---|
| Basic supplements | Growth factor supplements |
| 20% M199 | 20 ng/ml insulin like growth factor-1 |
| 10 nmol/l retinoic acid | 10 ng/ml epidermal growth factor |
| 0.1 nmol/l triiodothyronine | 10 ng/ml fibroblast growth factor-2 |
| 5 µg/ml hydrocortisone | 0.25 ng/ml endothelin-1 |
| 10 µg/ml insulin | 1 µg/ml angiotensin-II |
| 5.5 mg/l transferrin | 10 ng/ml cardiotrophin-1 |
| 5 µg/l selenium | 10 ng/ml interleukin-1 β |
| 0.5 µg/l bovine serum albumin | 5 ng/ml transforming growth factor β 1 |
| 4.7 µg/ml linoleic acid | |
| 4.7 µg/ml oleic acid | |

Following the above protocols, it will also be possible to generate pouch-like constructs from cells of heart tissue other than cardiac myocytes. The skilled person will appreciate that constructs without cardiac myocytes will serve as a pure restraint device without providing any contractile support to the failing heart. In this regard, human mesenchymal stem cells, e.g. from the bone marrow, blood, heart tissue, or fat tissue (for example, islet-1, CD117 and/or CD105 positive) may be used as a starting material. Further, resident or circulating endothelial stem cells, for example, from the bone marrow or blood (e.g. CD133 and/or CD34 positive) may be used. Primary mesenchymal (e.g. vimentin, CD117 and/or CD105 positive) and endothelial (e.g. CD34 and/or CD31 positive) cells from the bone marrow, blood or heart tissue may also be used in this respect. According to a further aspect, fibroblasts, smooth muscle cells, and the like will serve as a starting material. For example, Zimmermann W H, et al. (2006), Nat Med, 12:452-458, describes the generation of engineered heart tissue (EHT) from fibroblasts (about 80%) and smooth muscle cells. Non-contractile cell fractions from enzymatically (trypsin/DNase) digested hearts were grown on standard culture dishes and propagated by serial plating. Subsequently, cells were detached from the culture dish by trypsin/EDTA treatment.

Following the above protocols, it will also be possible to generate pouch-like constructs from cells of heart tissue other than cardiac myocytes. The skilled person will appreciate that constructs without cardiac myocytes will serve as a pure restraint device without providing any contractile support to the failing heart. In this regard, human mesenchymal stem cells, e.g. from the bone marrow, blood, heart tissue, or fat tissue (for example, islet-1, CD117 and/or CD105 positive) may be used as a starting material. Further, resident or circulating endothelial stem cells, for example, from the bone marrow or blood (e.g. CD133 and/or CD34 positive) may be used. Primary mesenchymal (e.g. vimentin, CD117 and/or CD105 positive) and endothelial (e.g. CD34 and/or CD31 positive) cells from the bone marrow, blood or heart tissue may also be used in this respect. According to a further aspect, fibroblasts, smooth muscle cells, and the like will serve as a starting material. For example, Zimmermann W H, et al. (2006), Nat Med, 12:452-458, describes the generation of engineered heart tissue (EHT) from fibroblasts (about 80%) and smooth muscle cells. Non-contractile cell fractions from enzymatically (trypsin/DNase) digested hearts were grown on standard culture dishes and propagated by serial plating. Subsequently, cells were detached from the culture dish by trypsin/EDTA treatment. Dispersed cells (250,000-10,000,000, ideally 2,500,000 were mixed with collagen and concentrated culture medium according to the protocol published in Zimmermann et al. 2002 Circ Res. MATRIGEL™ is not necessary to generate non-contractile tissue constructs. Culture is performed according to the published protocol. It must be understood that many cell types including fibroblasts from heart biopsies from mammals including humans, fat tissue-derived mesenchymal stem cells (from liposuction samples) from mammals including humans as well as endothelial cells, smooth muscle cells, pluripotent stem cells and others can be applied to generate non-contractile tissue constructs that can be applied as restraint devices. Additional benefit may stem from paracrine factors, e.g., growth promoting factors, angiogenic factors or antiapoptotic factors. Examples for such factors include, but are not limited to, VEGF, HGF, PLGF PDGF, CT-1, FGF, SDF-1, HCG, IGF-1, BMP and others. These factors could induce angiogenesis, support heart cell survival, induce cell proliferation or hypertrophic growth.

According to a particular preferred embodiment of the invention, the cells which are used for preparing the pouch-like constructs of the invention are derived from the patient who shall receive the construct in order to prevent or ameliorate distension and/or resisting dilation of the heart. Accordingly, the construct will essentially consist of tissue that originates from the patient to be treated.

As outlined above, stem cells of different mammalian origin are also a suitable source for generating pouch-like tissue constructs comprising cardiac myocytes. Pluripotent embryonic stem cells may be used for preparing the pouch-like tissue constructs of the invention. However, other types of stem cells, such as pluripotent adult stem cells may also be used. The preparation of contractile tissue constructs derived from human stem cells is particularly described in the example part of the present invention. This protocol can be applied to the novel molding method of the present invention.

The invention further provides a method for the preparation of the above-described pouch-like construct. Thus according to a separate aspect of the invention, a method for the preparation of a pouch-like construct suitable for enclosing at least part of the heart of a mammal and comprising engineered tissue comprises the following steps:
  a) providing a matrix having a recess in one surface of the matrix, which recess has dimensions corresponding to the desired dimensions of the exterior of the pouch-like construct to be formed.

b) providing a body having dimensions corresponding to the desired dimensions of the interior of the pouch-like construct to be formed, c) disposing the body in the recess of the matrix such that the body is spaced from the walls of the recess to form a space between the body and the walls of the recess corresponding to the desired dimensions of the construct.

d) disposing a reconstitution mixture in the recess, which reconstitution mixture comprises mammalian cells and suitable scaffold material which can be incubated to form an engineered tissue construct, e) contacting the reconstitution mixture disposed within the recess with a culture medium suitable for culturing the cells in the reconstitution mixture.

f) incubating the reconstitution mixture until the tissue construct forms within the matrix recess between the body and the matrix until a tissue construct is formed, g) removing the body with the tissue construct adherent thereto from the matrix recess, and h) separating the tissue construct from the body.

Thus, according to the method, a matrix with a recess in one surface and a body are provided, the body is disposed in the recess, and a reconstitution mixture is introduced into the recess in order to form the pouch-like construct from the tissue cells of the reconstitution mixture in the space between the outer surface of the body and the inner surface of the matrix walls defining the recess. The matrix together with the body serves as a mold. As used herein, the term matrix designates any body having a recess or cavity used for shaping an object or material and is e.g. a mold or part of a mold.

Within the meaning of the present invention, the term "reconstitution mixture" designates a mixture comprising mammalian cells and suitable scaffold material which can be incubated to form an engineered tissue construct. Reconstitution mixtures for generating engineered heart tissue are exemplified in the prior art mentioned above.

Figure 1:
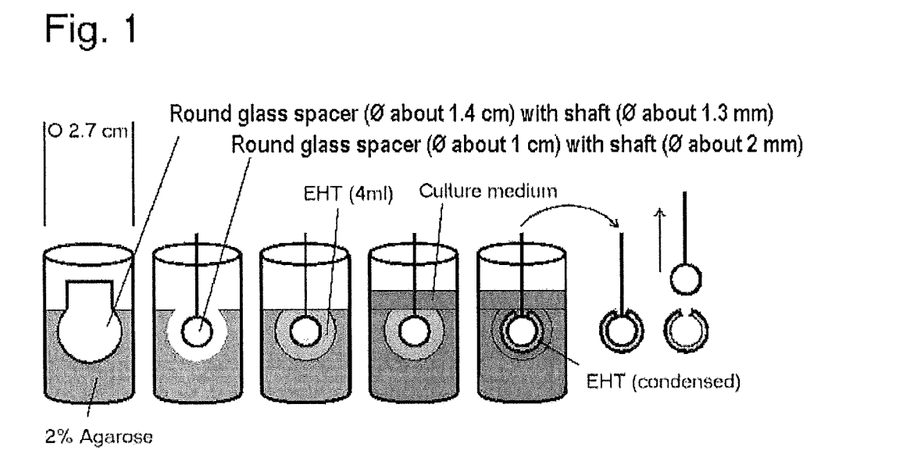
FIG. 1 shows a schematic depiction of the method for preparing the pouch-like tissue construct according to the invention.

While the recess has dimensions which correspond to the dimensions of the exterior of the desired pouch-like construct, the body to be disposed in the recess has dimensions corresponding to the desired dimensions of the interior of the construct. In other words, by choosing the dimensions of the body in relation to the dimensions of the recess, the available space for introducing the tissue reconstitution mixture which forms the pouch-like construct is determined. The person of skill will have no problems in changing the space between the body and the walls defining the recess of the matrix in order to adjust the volume of the tissue reconstitution mixture, that he intends to apply, to a particular application. For example, when the preparation of a pouch-like construct for use as a support device of a rat heart is sought, body and recess can be chosen to have a spherical shape or the shape of a segment of a sphere. As shown in FIG. 1, a matrix recess having the shape of a segment of a sphere with a diameter of 14 mm and a spherical body having a diameter of 10 mm may be used. The body is disposed in a spaced relationship with respect to the walls defining the recess. Preferably it is disposed in the recess such that the radial distance between the body and the walls defining the recess is essentially uniform, i.e. approximately the same at each location within the space, which means that the radial distance is about 2 mm. In this manner, it was possible to dispose about 4 ml of tissue reconstitution mixture in the space between the body and the walls of the recess.

The dimensions of the space between the body and the walls of the recess determine the dimensions of the pouch-like construct formed. The concrete design chosen for the recess of the matrix depends on the size of the heart to be treated with the tissue construct. For example, if the pouch-like construct is intended for supporting a human heart, it should have a length of about 50-200 mm, preferably of about 80-150 mm, and more preferably or 100-120 mm, wherein the length is measured from the center of the bottom of the pouch-like construct to the center of the opening of the pouch-like construct.

For disposing the mixture for the reconstitution of the tissue construct in the recess, in the easiest embodiment the reconstitution mixture is prepared and subsequently pipetted into the recess of the matrix. Of course, it is also possible to directly add the distinct components of the reconstitution mixture into the recess and to thoroughly mix these components by repeatedly pipetting.

The method further comprises contacting the reconstitution mixture within the recess with a culture medium that is suitable for culturing cells in the mixture such that they can form the construct. Accordingly, the matrix used for the preparation of the pouch-like construct can be any matrix which allows a suitable contact between the tissue reconstitution mixture in the recess of the matrix and a medium used for culturing the tissue construct during its formation.

After the body and the reconstitution mixture have been disposed in the recess in the above manner and the reconstitution mixture has been brought into contact with a culture medium, the arrangement is incubated for 3 to 50 days, preferably 10-30 days, and more preferably 12 to 20 days until the tissue construct has been formed around and on the outside of the body. As outlined above, the same media as used within the reconstitution mixture can be used during this incubation period. Suitable culturing conditions are described in the art and comprise a physiological temperature range of 30-40.degree. C., preferably 36-38.degree. C., and more preferably 37.degree. C. The percentage of $O_2$ in the ambient air should range from 21-80%, preferably 70%, 60% 50%, and more preferably 40%.

In this connection it is to be understood that the step of contacting the reconstitution mixture with a culture medium does not have to be performed prior to the step of incubating the reconstitution mixture. It is also possible that the contacting step is performed during the incubating step or between two parts of the incubating step. For example, it is preferred that the reconstitution mixture is incubated without being in contact with a culture medium for a first period of time of e.g. 1 h until the reconstitution mixture solidifies or hardens to some extent, e.g. into a semi-solid, and that only this reconstitution mixture of increased viscosity is contacted with a culture medium. Following this contacting step, a further incubation period is performed for the above-mentioned periods of time.

Following formation of the construct within the recess, the body is removed from the recess together with the construct adhering to the body. Then, the construct is separated and removed from the body without damaging the construct. The isolated construct may then be stored in an appropriate culture medium until use. Such culture medium may include, for example, (DMEM, 10% horse serum, 2% chick embryo extract, 100 U/ml penicillin, 100 µg/ml streptomycin).

According to a preferred embodiment, the step of providing a matrix includes providing a porous matrix, the pores of which are at least partially filled with a liquid in order to impede outflow of reconstitution mixture from the recess into the porous matrix by blocking outflow paths. The step of contacting the reconstitution mixture disposed within the recess with a culture medium includes disposing a liquid culture medium on the surface of the matrix in which the recess is formed. In this way, a layer is formed on this surface of the matrix that covers this surface including the free surface of the reconstitution mixture in the recess. Subsequently, mixing between the layer of culture medium and the reconstitution mixture occurs via the boundary surface and/or by the culture medium moving into the pores of the matrix. A suitable matrix comprises or consists of agarose, alginates, Agar or PEG. For a agarose matrix, the agarose content can be adjusted (2-10%) to alter culture medium perfusion throughout the mold.

In an alternative embodiment, a porous or non-porous matrix can be provided which already contains the culture medium which is to be used for culturing the tissue constructs in solid, semi-solid or liquid form throughout the entire matrix or at least in the regions adjacent the recess. For example, an agarose matrix may be prepared by mixing dissolved agarose with concentrated culture medium (e.g. addition of 2×DMEM, 20% horse serum, 4% chick embryo extract, 200 U/ml penicillin, 200 µg/ml streptomycin to 4% agarose yields a final mixture containing 2% agarose in culture medium). Care has to be taken to add the sterile culture medium components to solubilised agarose, e.g. at 40-60° C. Hardening will occur after incubation at room temperature. Of course, it is also possible to combine aspects of these two embodiments, e.g. by using a porous, liquid-filled matrix which includes a culture medium and by disposing a layer of liquid culture medium on top of the matrix surface.

The body used for establishing the interior of the pouch-like construct preferably has a spherical shape. Further, it is constructed such that at least a surface layer of the body is made of a material that is inert with respect to the reconstitution mixture and allows for readily separating the pouch-like construct from the body once the construct has formed. It is preferred that the body comprises a surface layer of glass, stainless steel, polytetrafluoroethylene (PTFE) (TEFLON®), polyoxymethylene (POM) (DEL-RIN®) or silicone. Even more preferably, the entire body consists of one or more of these materials. For example, the body can be a glass ball.

It is to be understood that disposing the body in the recess might be performed by disposing the entire body in the recess or by disposing only part of the body in the recess with the remainder of the body projecting out of the recess. In the latter case, the pouch-like construct, of course, only forms on and about the portion of the body disposed in the recess. Further, the remainder of the body projecting out of the recess may be used to manipulate or mount the body.

The body can be mounted on a rod-shaped portion. The rod-shaped portion can be used to connect the body with a fixture by means of which the position of the body within the recess of the matrix can be set and precisely maintained throughout the formation of the construct on the body.

In a further preferred embodiment, the body is an inflatable structure, such as an inflatable balloon which is connected with means for effecting a precisely controlled inflation of the body. By controlled inflation, for example by using a suitable pump, the dimensions of the balloon forming the body can be precisely adjusted, so that the space between the body and the walls of the recess and, ultimately, the wall thickness and the interior dimensions of the engineered tissue construct can be adapted to a particular application. The balloon can be made of silicone or similar flexible inert materials and can be filled with water, mineral oil or air connected to a pump to inflate the balloon. Further, the balloon may be inflated and deflated during or after the formation of the construct at a given rate (e.g. 1-10 Hz) and rhythm (e.g. sinus rhythm). This would allow simulation of physiological loading and unloading of a ventricle and can (1) improve the morphological and functional properties of the tissue constructs and (2) allow force measurements by detecting the pressure change in the balloon developed by the spontaneously contracting tissue constructs.

In the method according to the invention, it is irrelevant whether the body or the reconstitution mixture is disposed in the recess first. Thus, either the body is introduced into the recess after a suitable quantity of reconstitution mixture was filled into the recess, or the space between the body and the walls of the recess is filled with a suitable amount of reconstitution mixture after the body was put in position within the recess.

According to a particularly preferred embodiment, the pouch-like constructs obtained from the surface of the body in step h) are further processed by culturing the constructs under tensile stress. According to a preferred embodiment of the invention, tensile stress is applied in a static, phasic or auxotonic manner or a combination thereof, Tensile stress can be performed for example by actively stretching the engineered tissues, for instance by use of a mechanical stretching device like the one described in Zimmermann, W. H. et al. Circulation Res 90, 223-30 (2002). Such device can provide for a "static" load, i.e. a permanent load produced by expanding the tissue construct by 3 to 20%, preferably 10%, of its original length (original length determined in the absence of any load) as described in WO 01/55297. Alternatively, a "phasic" load can be applied by periodically expanding the tissue construct by 3 to 20%, preferably 10% of its original length, for example at a frequency of 0.1-10 Hz, preferably 1-5 Hz.

According to a particularly preferred embodiment of the invention, the tensile stress is auxotonic stress. Applying "auxotonic stress", as used herein, means that the engineered tissue constructs are kept under conditions so that they have to contract against a defined force and are reexpanded during relaxation by another force or, preferably, the same force. For example, if the construct is held under tension by using a spring, this spring will provide a defined force against which the engineered heart tissue constructs must contract. Upon relaxation of the heart tissue constructs, the spring will expand the tissue constructs. It has been found that culturing the engineered heart tissue constructs in this manner leads to a considerable increase of contractile properties compared to phasic and static processes. Therefore, the pouch-like engineered heart tissue constructs show improved maximal active forces during contraction. Under auxotonic load, the tissue constructs have to perform contraction under conditions which resemble the systole and diastole phase of the heart cycle. In other words, the tissue constructs are held under conditions which corresponds to the native environment of active heart tissue. Devices that might be used for culturing engineered tissue constructs under tensile stress are described elsewhere in the art, for example in WO 01/55297, European application 05400038.5, and in Zimmermann W H, et al. (2006), Nat Med, 12:452-458. In accordance with these disclosures, the person of skill will be able to provide means for applying tensile stress to the pouch-like constructs of the present invention. The pouch-like constructs can be suspended in or on a suitable device, such as an inflatable and deflatable balloon. A suitable device is shown in the middle panel of FIG. 2. Alternatively, tensile stress may be applied to the constructs of the invention by placing the constructs on an inflatable balloon.

In several publications, it was demonstrated that contractile properties of artificially synthesized heart tissue can be improved by mechanically stretching the tissues after casting (see Eschenhagen et al., 2002; Fink et al., 2000; Zimmermann et al., 2002b). It has been demonstrated that mechanical load improves both orientation and differentiation of muscle cells in engineered tissues. Tensile stress can be applied for a period of time ranging from several hours to more than 40 days. Preferably, tensile stress is applied for 5-9, more preferably 7 days. During imposing tensile stress, the engineered tissues are cultured under the conditions as described above.

According to a further aspect, the invention relates to a method of treating a disease which is associated with dilation of the heart of a mammal. The treatment comprises steps in which the pouch-like construct of the invention is applied to the surface of the heart in order to prevent distension and/or resisting dilation of the heart. Preferably, the mammal is a human. The invention further relates to the use of the pouch-like construct of the invention for preventing distension and/or resisting dilation of a mammalian heart, preferably of a human heart.

According to a further aspect, the invention relates to the use of the pouch-like construct of the invention for drug target validation and drug development. According to a preferred embodiment, the pouch-like construct is used in drug screening or target validation assays. In this context, it is preferred that the pouch-like construct used is derived from a mammal, such as a human. For example, the pouch-like construct can be used to analyze the capability of candidate drugs to interfere with the physiological function of the native cardiac tissue of a mammal. For this, the capability of said candidate drug to enhance or reduce contractile functions of the pouch-like construct is determined. Moreover, the pouch-like construct may be used in determining the influence of the activity of certain genes on the physiological function of the native cardiac tissue of a mammal (referred to herein as target validation). For this purpose, genes of the cells within the constructs (or cells which are used for preparing the same) may be knocked-out or overexpressed or otherwise influenced in view of their expression rate (e.g., by addition of inhibitory molecules, such as small interfering RNAs). Genes may be selectively switched on or off, and the alterations in the contractile functions of the pouch-like construct are determined.

Examples

Statistical Analysis

Data are presented as mean±standard error of the mean. Statistical differences were determined using a repeated ANOVA (contraction experiments). A P value of <0.05 was considered statistically significant.

Methods and Materials

All procedures were approved by the local animal protection authority (BWG of the Freie and Hansestadt Hamburg: #54/04) and conformed to the Guide for the Care and Use of Laboratory Animals (NIH publication 86-23, revised 1996).

Cell Isolation

Figure 2:
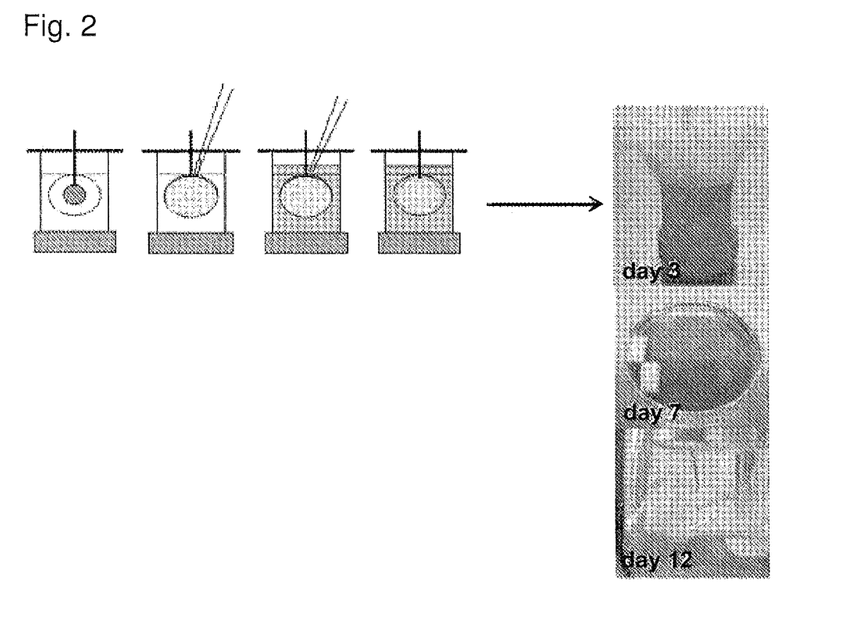

Cardiac myocytes were isolated from neonatal Wistar rats (postnatal on day 0-3) by a fractionated DNase/Trypsin digestion protocol as described in Zimmermann W H et al. (2000), Biotechnol Bioeng, 68:106-14. The resulting cell population which consisted of approximately 50% cardiomyocytes and 50% non-myocytes (Naito H, et al. (2006). Circulation 114:172-8) was immediately subjected to EHT generation Construction of a Casting Mold for a Pouch-Like Construct A novel casting mold was developed to facilitate the construction of pouch-like engineered tissue (FIGS. 1 and 2). Briefly, the pointed tip of a sterile 50 ml polypropylene tube with a screw cap (#62.547.004; Sarstedt, Germany) was cut off under sterile conditions. Subsequently, a round glass spacer (diameter: 14 mm) connected to a shaft (diameter: 13 mm) was placed into the tube. Subsequently, sterile 2% agarose, either in phosphate buffered solution or in serum-containing culture medium (DMEM, 10% horse serum, 2% chick embryo extract, 100 U/ml penicillin, 100 µg/ml streptomycin) were filled into the tube. The agarose was allowed to solidify. Thereafter, the glass spacer was removed leaving a hollow circular space in the agarose block. Another round glass spacer was then inserted into the hollow space to construct the final casting mold. This spacer had a diameter of approx. 10 mm with a thin shaft of a diameter of 2 mm). The described set-up was assembled under sterile conditions.

Figure 3:
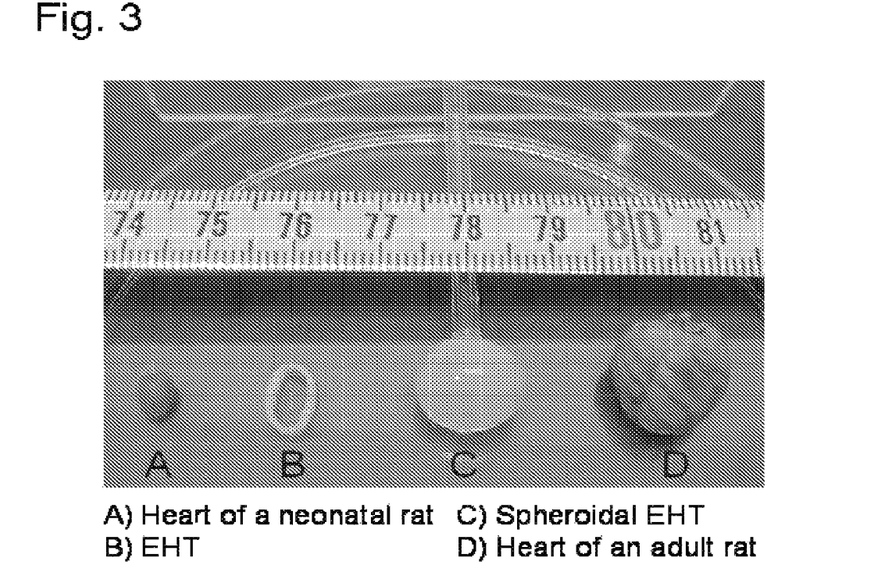
FIG. 3 shows a pouch-like tissue construct prepared from rat cardiac myocytes according to the method of the invention. (A) shows the heart of a neonatal rat; (B) shows a ring-shaped tissue construct prepared from rat cardiac myocytes according to a method described in WO 01/55297; (C) shows a spheroidal pouch-like tissue construct according to the invention; (D) shows the heart of an adult rat.
Figure 4:
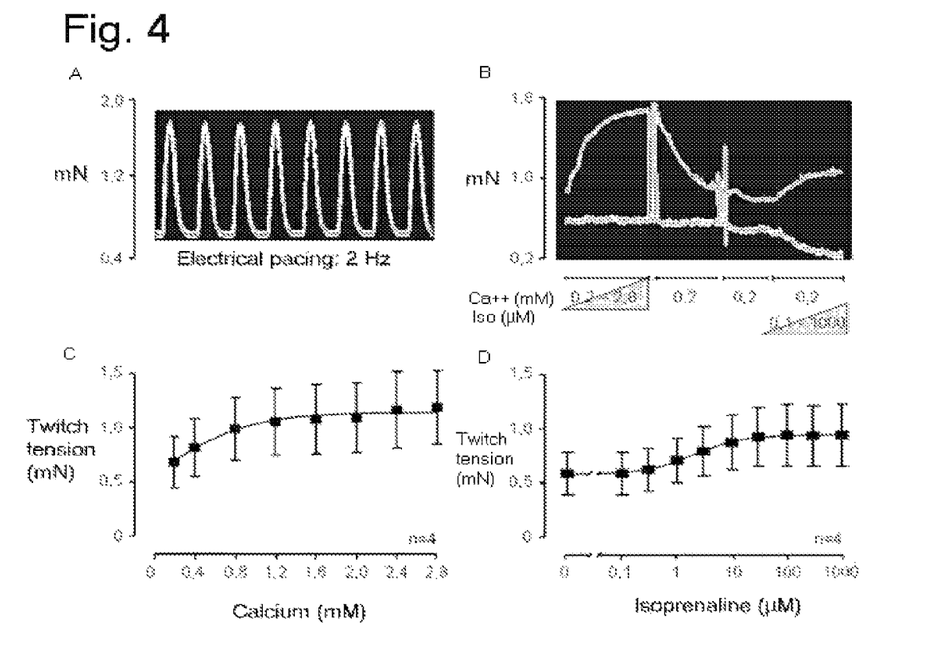
FIG. 4 shows the contraction experiments conducted with the pouch-like tissue construct according to the invention.

Generation of Pouch-Like Constructs 4 ml of an engineered heart tissue reconstitution mixture containing $10 \times 10^6$ freshly isolated neonatal rat heart cells (approximately 50% cardiomoycytes and 50% non-myocytes), 3.2 mg solubilized collagen type 1, MATRIGEL™ (10% v/v) and concentrated culture medium (2× DMEM, 20% horse serum, 4% chick embryo extract, 200 U/ml penicillin, 200 □g/ml streptomycin; to adjust the culture medium concentration in the complete reconstitution mixture to 1× DMEM, 10% horse serum, 2% chick embryo extract, 100 U/ml penicillin, 100 □g/ml streptomycin) was pipetted into the mold MATRIGEL™ can be replaced by Insulin (10 □g/ml) and triiodothyronine (1 nM) as described earlier (Naito H, et al. (2006). Circulation, 114:1 72-8). The engineered tissues were then incubated for 1 h at 37° C. in a humidified cell culture incubator (10% $CO_2$ in room air) to facilitate hardening of the reconstitution mixture. Subsequently, culture medium (DMEM, 10% horse serum, 2% chick embryo extract, 100 U/ml penicillin, and 100 □g/ml streptomycin) was carefully added to not disturb the reconstitution mixture. The agarose mold allowed free diffusion of culture medium throughout the casting mold enabling unrestricted supply with nutrients and oxygen to the reconstitution mixture. The engineered heart tissue condensed within 3-7 days and started to contract spontaneously. The constructs maintained their spontaneously contractions (1-2 Hz) throughout the experiments for at least 14 days. Spontaneously beating engineered heart tissue were transferred onto flexible holders to facilitate auxotonic contractions on culture day 7. Analyses of morphological and contractile properties of the constructs were examined after 12-14 culture days. The size of the construct was eventually comparable to the size of a native adult rat heart (FIG. 3), Isometric Force Measurements Force of contraction (twitch tension: TT), resting tension (RT), and contraction kinetics (contraction time: T1; relaxation time: T2) of the engineered tissues were analysed under isometric conditions and electrical stimulation in standard organ baths as previously described (Zimmermann W H, et al. (2002), Circ Res, 90:223-30). Inotropic and lusitropic responses to calcium (0.2-2.8 mmol/1) and isoprenaline (0.1-1000 nmol/l) of the pouch-like constructs were analysed and compared to native myocardium (Zimmermann W H, et al. (2002), Circ Res, 90:223-30). The pouch-like tissue constructs could be stimulated in a electrical field (0.5-6 Hz; FIG. 4A demonstrates contraction amplitudes of electrical stimulated [at 2 Hz] constructs) and demonstrated a baseline twitch tension of 0.7±0.2 mN at 0.2 mmol/1 calcium (n=4). Addition of calcium and isoprenaline increased twitch tension to 1.2±0.3 mN and 0.9±0.3 mN, respectively (n=4; FIG. 4C+D). FIG. 4B shows an original tracing of a contraction experiment (upper and lower lines indicate maximal [systolic] and minimal [diastolic] force of pouch-like constructs. Taken together; pouch-like engineered heart tissue show contractile properties of native mammalian myocardium.

Morphologic Evaluation of the Engineered Heart Tissues

Formaldehyde fixed engineered heart tissues were embedded in paraffin, sectioned, and stained with hematoxylin and eosin (H&E) for light microscopic evaluation or processed for LSM as described previously in Zimmermann W H, et al. (2002). Circ Res, 90:223-30. Specific labelling of α-sarcomeric actinin and sarcomeric actin, CD31, and prolylhydroxylase was employed with appropriate secondary antibodies to identify cardiomyocytes, enothelial cells, and fibroblasts in the engineered heart tissues. Confocal laser scanning analyses were performed with a Zeiss LSM 510 META system.

The pouch-like tissue constructs contained a highly interconnected network of differentiated cardiomyocytes. Cells were interconnected through connexin 43 suggesting electrical coupling and formation of a functional syncytium., Notably, the surface of the engineered heart tissues was covered by a dense epithelium consisting of prolyl-hydroxylase positive cells suggesting that fibroblast-like cells formed a pseudo-epi/endocardium, CD31 and lectin staining demonstrated the formation of capillary like structures throughout the engineered heart tissues, Implantation of Engineered Heart Tissues The engineered heart tissues were implanted in male Wistar rats (n=10; 300-350 g). Anaesthesia was induced in an induction chamber filled with isoflurane (4%) and maintained after incubation and continuous ventilation with room air supplemented and isoflurane (1%) throughout the surgery as described earlier in Zimmermann W H, et al. (2006), Nat Med, 12:452-458.

Figure 5:
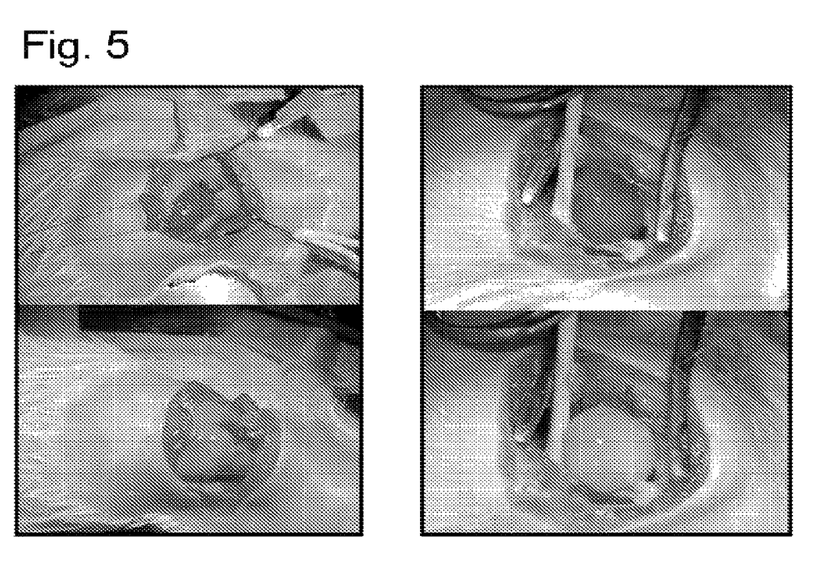
FIG. 5 shows the implantation of the pouch-like tissue construct in Wistar rats.
Figure 6:
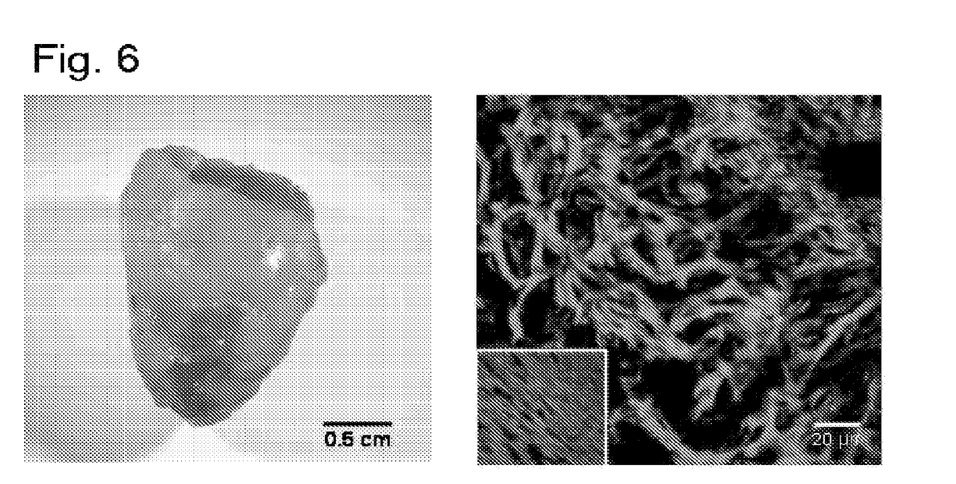
FIG. 6 shows the morphology of the pouch-like tissue construct after implantation into Wistar rats. On the left panel, the pouch-like tissue construct is shown on a rat heart explanted after two weeks. On the right panel, the surviving of cardiac myocytes after two weeks is shown as controlled by confocal laser scanning analyses using DNA and actin labelling techniques (DAPI and phalloidin-Alexa 488, respectively).

The thoracic cavity was opened through a bilateral thoracotomy (FIG. 5A) or left lateral thoracotomy (n=10; FIG. 5B). The hearts were exposed after excision of the pericardium. The engineered heart tissue construct was slipped over the entire left and right ventricles from apex to base and fixed with two sutures (5-0 ETHIBOND®, Ethicon) at the anterior and lateral base of the beating hearts, TARDOMYOCEL® (12,500 IU penicillin/kg and 15.5 mg streptomycin/kg, intramuscular injection; Bayer) and buprenorphine hydrochloride (0.1 mg/kg, intraperitoneal injection) were injected during surgery, Cyclosporine A (5 mg/kg), azathioprine (2 mg/kg), and methylprednisolone (2 mg/kg) were administered daily by subcutaneous injection for immune suppression. All animals survived this procedure, 14 days after implantation, we could clearly identify the engrafted pouch-like engineered heart tissues on the heart (FIG. 6; left panel). Moreover, confocal laser scanning analyses indicated that morphological structures of native myocardium were maintained in engrafted engineered heart tissues (FIG. 6; right panel). In addition, vascularization of engrafted tissue constructs was observed.

Engineered Tissue Construction from Human Embryonic Stem Cells

Suitable ES Cell Lines

Pluripotent human embryonic cell lines have been established and can be commercially obtained from different providers. These cell lines have been listed by the US National Institutes of Health (Bethesda, Md., USA), from which further information as to the cell line characteristics and providers may be obtained. The following ES cell lines are available and may be used for preparing engineered heart tissue: cell lines hESEGN-01, hESBGN-$O_2$, hESBGN-03 from BresGen, Inc. (Athens, USA), NIH Code: BG01, $BGO_2$, BG03; cell lines Sahlgrenska 1, Sahlgrenska 2 from Cellartis AB (Goteborg, Sweden), NIH Code: SA01, $SAO_2$; cell lines HES-1, HES-2, HES-3, HES-4, HES-5, HES-6 from ES Cell International (Singapore), NIH Code: ES01, $ESO_2$, ES03, ES04, ES05, ES06; cell line Miz-hES1 from the Medical Research Center, MizMedi Hospital (Seoul, Korea), NIH Code: MI01; cell lines I 3, I 3.2, I 3.3, I 4, I 6, I 6.2, J 3, J 3.2 from the Rambam Medical Center (Haifa, Israel), NIH Code: TEO3, TE32, TE33, TE04, TE06, TE62, TE07, TE72; cell lines HSF-1, HSF-6 from the University of California, Department of Obstetrics, Gynecology & Reproductive Sciences (San Francisco, USA), NIH Code: UC01, UC06; cell lines H1, H7, H9, H13, H14 from the Wisconsin Alumni Research Foundation (Madison, USA), NIH Code: WA01, WA07, WA09, WA13, WA14.

Different groups have shown that human embryonic stem cell lines WA01 (H1), WA07 (H7), WA09 (H9) including subclones H9.1, H9.2 and $ESO_2$ can differentiate either spontaneously or if co-cultured with visceral-endoderm like cells (END-2) or liver parenchymal carcinoma cells (HepG2) into cardiac myocytes (Xu, C., et al. Characterization and enrichment of cardiac myocytes derived from human embryonic stem cells. Circ Res 91, 501-8 (2002); Kehat, I, et al. supra; Mummery, C. et al. Differentiation of human embryonic stem cells to cardiac myocytes: role of co-culture with visceral endoderm-like cells. Circulation 107, 2733-40 (2003)). However, the propensity of mammalian embryonic stem cells to differentiate into cardiac myocytes is an inherent trait of all true embryonic stem cells and thus not limited to the above mentioned cell lines. Apart from embryonic cells, other stem cells may be used for preparing the engineered tissue constructs according to the invention. Such stem cells include, but are not limited to, human pluripotent adult stem cells with a propensity to give rise to cardiac myocytes (e.g. c-kit positive cells (Beltrami et al. Cell 2003), endothelial progenitor cells (Badorff et al. Circ Res 2002), side population cells (Jackson et al. JCI-200.times.), Sca-1 positive cells (Oh et al. 2002), Is1-1 positive cells (Laugwitz et al. 2005). These cells may be derived from the blood, bone marrow or from various organs including the heart, the liver, umbilical cord, placenta, fat tissue, among others.

It is particularly preferred to employ genetically modified human embryonic stem cells for reconstitution of engineered heart tissue, e.g., cells capable of expressing proteins that allow selection of cardiac myocytes and/or depletion of non-myocytes. By selecting ES, homogenous cell populations can be formed which may again be substituted with defined and also selectable non-myocytes which include, but are not limited to, endothelial cells, fibroblasts, smooth muscle cells, and macrophages within the engineered heart tissue. Moreover, selection allows for depletion of tumorigenic cells which is a prerequisite for the use of the engineered heart tissues in therapeutic approaches, Selection can be performed before or simultaneously with reconstitution of the cells. For instance, in vitro-differentiation may be performed directly after propagation of the ES cells and the resulting embryonic stem cell derived cardiac myocytes can be subjected to selection before reconstituting the engineered heart tissue. Alternatively, undifferentiated embryonic stem cells are propagated and used for the preparation of engineered heart tissue constructs and selection is performed on the constructs at a later stage. Preferably, selection is to be performed after the constructs have been formed.

Selection may be achieved by stable introduction of selectable marker genes. The expression of such genes is controlled either by a cardiac myocyte specific promoter (positive selection) or a non-myocyte specific promoter (negative selection) into embryonic stem cells. These may be but are not limited to:

- amino-3' glycosyl phosphotransferase conferring a neomycin resistance [neoR]
- herpes simplex virus thymidine kinase [TK] which transforms ganciclovir into a cytotoxic triphosphate
- purine nucleoside phosphorylase [PNP] from *Escherichia coli* which converts fludarabine to toxic fluoro-ATP
- fluorescing proteins and β-galactosidase which facilitate optical identification Expression of neoR, fluorescing proteins, or β-galactosidase under the control of a cardiac myocyte specific promoter, e.g. .alpha.-myosin heavy chain promoter (see Klug, M. G., Soonpaa, M. H., Koh, G. Y. & Field, L. J. Genetically selected cardiac myocytes from differentiating embryonic stem cells form stable intracardiac grafts. J Clin Invest 98, 216-24 (1996)), myosin light chain 2v promoter (see Muller, M. et al. Selection of ventricular-like cardiac myocytes from ES cells in vitro. Faseb J 14, 2540-8 (2000)) enable positive selection of cardiac myocytes by eliminating non-myocytes either through addition of cytotoxic G418 or fluorescence activated cell sorting (FACS).

The techniques for selection are well known to the person of skill. Alternatively, non-myocytes expressing TK or PNP under the control of a promoter that is not active in cardiac myocytes, e.g. the Oct-4 promoter (Boiani, M., Kehler, J. & Scholer, H. R. Activity of the germline-specific Oct4-GFP transgene in normal and clone mouse embryos. Methods Mol Biol 254, 1-34 (2004)), the Rex-1 promoter (see Hosier, B. A., Rogers, M. B., Kozak, C. A. & Gudas, L. J. An octamer motif contributes to the expression of the retinoic acid-regulated zinc finger gene Rex-1 (Zfp-42) in F9 teratocarcinoma cells. Mol Cell Biol 13, 2919-28 (1993)) can be eliminated (negative selection) by addition of ganciclovir or fludarabine, respectively (Lockett, L. J., Molloy, P. L., Russell, P. J. & Both, G. W. Relative efficiency of tumor cell killing in vitro by two enzyme-prodrug systems delivered by identical adenovirus vectors, Clin Cancer Res 3, 2075-80 (1997)). Genetic modification of human embryonic stem cells is either performed by stable transformation utilizing established lipofection or electroporation protocols to introduce the genetic information [cDNA] into stem cells (see, for example, Nagy, A., Gertsenstein, M., Vintersten, K. & Behringer, R. Manipulating the Mouse Embryo: A Laboratory Manual. (2002); Eiges, R. et al. Establishment of human embryonic stem cell-transfected clones carrying a marker for undifferentiated cells. Curr Biol 11, 514-8 (2001)) or by lentivirus mediated gene transfer leading to stable transduction of embryonic stem cells (see Ma, Y., Ramezani, A., Lewis, R., Hawley, R. G. & Thomson, J. A. High-level sustained trans-gene expression in human embryonic stem cells using lentiviral vectors. Stem Cells 21, 111-7 (2003)). Integration of the exogenous genetic material is confirmed by standard methods (e.g., southern blotting, polymerase-chain-reaction; see Sambrook, J. & Russell, D, Molecular Cloning: A Laboratory Manual. (2001)).

Preparing EHTs from Selectable, Undifferentiated ES Cells

Selectable human embryonic stem cells are used for reconstitution in an undifferentiated state. The undifferentiated human embryonic stem cells are cultured for propagation in Dulbecco's modified Eagle's medium (DMEM) with 20% batch tested fetal calf serum or 20% serum replacement, 1 mM L-glutamine, 0.1 mM β-mercaptoethanol, and 1% nonessential amino acids on mitotically inactivated fibroblast feeders (see Xu, C., et al. supra; Kehat, I. et al., supra) until a sufficient cell number of about $0.1\text{-}10 \times 10^6$ cells is reached. All substances are provided by several companies including INVITROGEN™. Human basic fibroblast growth factor (bFGF, 4 ng/ml) is not essential but may be added to improve maintenance of an undifferentiated state, Antibiotics (100 U/ml penicillin and 100 μg/ml streptomycin) may also be added. Subsequently, undifferentiated selectable embryonic stem cells ($0.1\text{-}10 \times 10^6$ cells) are mixed with scaffold material (e.g. collagen type I, concentration: 0.5-1.5 mg/ml) and growth promoting culture medium (see above). The total reconstitution volume consists normally of 0.5-1 ml but may be reduced or increased depending on the respective demand. The reconstitution mixture is filled into casting molds (e.g. the circular molds described in the WO 01/55297 or the novel mold disclosed in the present invention) immediately after mixing. Under normal culture conditions (e.g. 37° C., 5-10% $CO_2$, 21-40% $O_2$) solid tissue-like structures will form within 1-10 days. Under these conditions, differentiation of the embryonic stem cells occurs spontaneously and may additionally be affected by exogenous factors (e.g. addition to the culture medium of growth factors and cytokines including insulin, insulin-like growth factor, cardiotrophin-1, bone morphogenic proteins, sonic hedgehog at $EC_{50}$ concentrations). The solid tissue-like structures may optionally be transferred on stretch devices (as described above) to optimize culture medium perfusion and impose defined mechanical strain—which may be static, phasic, or auxotonic—on the tissue constructs.

Positive or negative selection (see above) may be performed after formation of contractile areas within the engineered tissues 5-30 days after casting of the reconstitution mixture into the mold. Alternatively, selection may be performed after the constructs have been transferred to the stretching device. Selection may be performed until optimal tissue structure and function has developed (e.g. 10-40 days depending on the observed effect) Selection may be achieved by addition of a defined pharmacological agent (e.g. G418, ganciclovir, fludarabine) into the culture medium)

Preparing Engineered Tissue from ES-Derived Cardiac Myocytes

For the preparation of engineered heart tissue from human cells, we utilised cardiac myocytes derived from an established human embryonic stem cell line (H9, H9.2). However, it is to be understood that all true human and non-human embryonic stem cells can be used for preparing the engineered heart tissue of the invention. For example, human embryonic stem cells derived from individual blastomeres (Klimanskaya I, Chung Y. Becker S, Lu S J, Lanza R (2006) "Human embryonic stem cell lines derived from single blastomeres", Nature, electronic publication ahead of print on Aug. 23, 2006) or from the inner cell mass of an embryo in the blastocyst stage (Thomson J A et al. (1998), Science 282:1145-7) as well as other multipotent embryonic-stem cell like cells, e.g. from parthenogenetic embryos (Vrana K E et al. (2003). Proc Natl Acad Sci USA, 100 Suppl 1:11911-6), adult germline stem cells (Guan K et al. (2006), Nature 440:1199-203), somatic nuclear transfer derived embryos (Wakayama T et al. (2001), Science 292: 740-3) or reprogrammed somatic cells (Cowan C A, et al. (2005), Science 309:1369-7; Takahashi K and Yamanaka S (2006), Cell 126:663-76) can be used. Similarly, somatic stem cells (Badorff C, et al. (2003). Circulation 107:1024-32; Beltrami A P, et al. (2003), Cell 114:763-76; Dimmeler S, et al (2005); J Clin Invest 115:572-83; Murry C E, et al. (2005). Circulation 112:3174-83) with a cardiogenic potential are applicable in engineered heart tissue construction as outlined for embryonic stem cells. Embryonic stem cell derived cardiac myocytes were selected by micro-dissection after spontaneous differentiation in vitro. Differentiation was performed in suspension culture, and the cells were subsequently plated on gelatin-coated culture dishes as previously described by Kehat, I et al., J Clin Invest 108, 407-14 (2001). Beating clusters containing embryonic stem cell derived cardiac myocytes were excised with a sharp, sterile glass or plastic pipette. Prior to reconstitution, ES-cell derived cardiac myocytes were enzymatically dispersed in collagenase IV LIFE TECHNOLOGIES™, 1 mg/ml for 20 min) or with trypsin/EDTA, ES-cell derived cardiac myocytes (10.000-15×10$^6$ dispersed cells/500 □l reconstitution mix, preferably 20.000-250,000 dispersed cells/500 E I reconstitution mix) were reconstituted with collagen, MATRIGEL™ and culture medium according to the established protocol by Zimmermann W. H. et al. Circ Res 90, 223-30 (2002) and WO 01/55297, with the exemption that the following culture medium was used: DMEM (preferably containing 80% knock-out DMEM [no-pyruvate, high-glucose formulation. Inc LIFE TECHNOLOGIES™]), 20% fetal calf serum, 1 mM glutamine, 0.1 mM 3-mercaptoethanol, 1% non-essential amino acids. MATRIGEL™ can be replaced by a mixture of triidothyronine (1 nM) and insulin (10 □g/ml). The EHT reconstitution mixture was pipetted into circular casting molds as described and the mixture was incubated to allow hardening. First contractions of single cardiac myocytes were observed after 24 hours of human engineered heart tissue culture, larger cell accumulations within the human engineered heart tissue started to contract synchronously after approx. 1-3 days whereas in unison contractions of whole engineered heart tissues with 1-2 Hz were observed after approx 2-10 culture days.

The invention claimed is:

1. A pouch-like construct suitable for enclosing at least part of a heart of a mammal for reducing and/or preventing cardiac dilation,
   wherein the construct comprises engineered tissue, has contractile properties, and has a length of 50-200 mm as measured from the center of the bottom of the pouch-like construct to the center of the opening of the pouch-like construct, and
   wherein the construct is obtained by a method comprising the steps of:
   a) providing a matrix having a recess in one surface of the matrix, wherein said recess has desired dimensions corresponding to desired dimensions of an exterior of the pouch-like construct for the pouch-like construct's exterior to be formed;
   b) providing a body having dimensions corresponding to desired dimensions of an interior of the pouch-like construct for the pouch-like construct's interior to be formed;
   c) disposing the body in the recess of the matrix such that the body is spaced from walls of the recess to form a space between the body and the walls of the recess corresponding to the desired dimensions of the construct;
   d) disposing a reconstitution mixture in the recess, wherein said reconstitution mixture comprises mammalian cells and suitable scaffold material which can be incubated to form an engineered tissue construct, said construct comprising cardiac myocytes;
   e) contacting the reconstitution mixture disposed within the recess with a culture medium suitable for culturing the cells in the reconstitution mixture;
   f) incubating the reconstitution mixture until a tissue construct forms within the matrix recess between the body and the matrix;
   g) removing the body with the tissue construct adherent thereto from the matrix recess; and
   h) separating the tissue construct from the body.

2. The pouch-like construct according to claim 1, wherein the pouch-like construct consists of mammalian tissue.

3. The pouch-like construct according to claim 1, wherein more than 25% of volume of the construct consists of cardiac myocytes.

4. The pouch-like construct according to claim 2, wherein the mammalian tissue is human heart tissue comprising human cardiac myocytes.

5. The pouch-like construct according to claim 4, wherein the construct has a wall thickness of 1-8 mm.

6. The pouch-like construct according to claim 5, wherein the construct has a wall thickness of 2-3 mm.

7. The pouch-like construct according to claim 1, wherein the step of providing a matrix includes providing a porous matrix filled with a liquid in order to impede outflow of the reconstitution mixture from the recess into the porous matrix, and wherein the step of contacting the reconstitution mixture disposed within the recess with a culture medium includes disposing a liquid culture medium on the surface of the matrix in which the recess is formed in order to form a layer of the culture medium on top of the matrix and the reconstitution mixture disposed within the recess.

8. The pouch-like construct according to claim 1, wherein the step of providing a matrix includes providing a porous matrix including the culture medium.

9. The pouch-like construct according to claim 1, wherein the body is spherical.

10. The pouch-like construct according to claim 1, wherein the body comprises a surface of glass, polytetrafluoroethylene (PTFE), or silicone.

11. The pouch-like construct according to claim 1, wherein the body is an inflatable structure.

12. The pouch-like construct according to claim 1, wherein step c) is performed prior to step d).

13. The pouch-like construct according to claim 1, wherein step d) is performed prior to step c).

14. The pouch-like construct according to claim 1, wherein after step h), the construct is subjected to tensile stress.

15. The pouch-like construct according to claim 14, wherein the tensile stress is static, phasic or auxotonic stress, or a combination of any of static, phasic or auxonic stress.

16. The pouch-like construct according to claim 14, wherein the tensile stress is auxotonic stress.

17. The pouch-like construct according to claim 1, wherein the pouch-like construct has a length of 80-150 mm.

18. The pouch-like construct according to claim 1, wherein the pouch-like construct has a length of 100-120 mm.

* * * * *